United States Patent
Heidemann et al.

(10) Patent No.: US 6,586,361 B1
(45) Date of Patent: Jul. 1, 2003

(54) MULTILAYERED SHELL CATALYSTS FOR CATALYTIC GASEOUS PHASE OXIDATION OF AROMATIC HYDROCARBONS

(75) Inventors: Thomas Heidemann, Weinheim (DE); Stefan Bauer, Ludwigshafen (DE); Gerd Linden, Heidelberg (DE); Hermann Petersen, Grünstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/763,661

(22) PCT Filed: Aug. 17, 1999

(86) PCT No.: PCT/EP99/06012
§ 371 (c)(1),
(2), (4) Date: Feb. 26, 2001

(87) PCT Pub. No.: WO00/12214
PCT Pub. Date: Mar. 9, 2000

(30) Foreign Application Priority Data

Aug. 27, 1998 (DE) .......................... 198 39 001

(51) Int. Cl.⁷ ................................ B01J 23/18
(52) U.S. Cl. ................... 502/353; 502/209; 502/344; 502/350
(58) Field of Search ............... 502/208, 209, 502/350, 353, 344

(56) References Cited

U.S. PATENT DOCUMENTS

| | | | |
|---|---|---|---|
| 3,394,468 A | 7/1968 | Zeller | 34/57 |
| 3,565,829 A | 2/1971 | Friedrichsen et al. | 252/464 |
| 3,684,741 A | 8/1972 | Friedrichsen et al. | 252/435 |
| 3,799,866 A | 3/1974 | Felice et al. | 252/461 |
| 3,894,971 A | 7/1975 | Reuter et al. | 252/437 |
| 4,324,694 A | 4/1982 | Reuter et al. | 252/435 |
| 5,677,261 A | 10/1997 | Tenten et al. | 502/439 |
| 5,792,719 A | 8/1998 | Eberle et al. | 502/178 |

FOREIGN PATENT DOCUMENTS

| | | |
|---|---|---|
| DE | 1 280 756 | 4/1970 |
| DE | 1 642 938 | 5/1971 |
| DE | 1 769 998 | 2/1972 |
| DE | 2 106 796 | 8/1972 |
| DE | 2 212 964 | 9/1973 |
| DE | 197 07 943 A1 | 9/1988 |
| DE | 40 13 051 | 11/1991 |
| DE | 198 23 262 A1 | 12/1999 |
| DE | 198 24 532 A1 | 12/1999 |
| EP | 0 021 325 A1 | 1/1981 |
| EP | 0 286 448 A2 | 10/1988 |
| EP | 0 714 700 A2 | 6/1996 |
| EP | 0 744 214 A1 | 11/1996 |
| WO | WO 98/37967 | 9/1998 |

*Primary Examiner*—Stanley S. Silverman
*Assistant Examiner*—Edward M. Johnson
(74) *Attorney, Agent, or Firm*—Keil & Weinkauf

(57) ABSTRACT

A coated catalyst for the catalytic gas-phase oxidation of aromatic hydrocarbons comprises, on an inert nonporous support, a catalytically active composition comprising a defined amount of vanadium oxide, titanium dioxide, a cesium compound, a phosphorus compound, and antimony oxide, wherein the catalytically active composition is applied in two or more layers and where relative to the inner layer or inner layers the outer layer has an antimony oxide content which is from 50 to 100% lower and wherein the amount of catalytically active composition of the inner layer or layers is from 10 to 90% by weight of the amount of catalytically active composition, and can be used for preparing carboxylic acids and/or anhydrides, in particular phthalic anhydride; also specified is a production process for such catalysts.

12 Claims, No Drawings

MULTILAYERED SHELL CATALYSTS FOR CATALYTIC GASEOUS PHASE OXIDATION OF AROMATIC HYDROCARBONS

The present invention relates to a coated catalyst for the catalytic gas-phase oxidation of aromatic hydrocarbons, comprising, on an inert nonporous support, a catalytically active composition comprising, in each case based on the total amount of catalytically active composition, from 1 to 40% by weight of vanadium oxide, calculated as $V_2O_5$, from 60 to 99% by weight of titanium dioxide, calculated as $TiO_2$, up to 1% by weight of a cesium compound, calculated as Cs, up to 1% by weight of a phosphorus compound, calculated as P, and up to a total of 10% by weight of antimony oxide, calculated as $Sb_2O_3$. In addition, it relates to a production process for these catalysts and to a process using these catalysts for preparing carboxylic acids and/or anhydrides and especially phthalic anhydride.

It is known that many carboxylic acids and/or carboxylic anhydrides are prepared industrially by the catalytic gas-phase oxidation of aromatic hydrocarbons such as benzene, the xylenes, naphthalene, toluene or durene in fixed-bed reactors, preferably multitube reactors. These processes are used to obtain, for example, benzoic acid, maleic anhydride, phthalic anhydride isophthalic acid, terephthalic acid or pyromellitic anhydride. The usual procedure is to pass a mixture of a gas comprising molecular oxygen, for example air, and the starting material to be oxidized through a plurality of tubes arranged in a reactor, with a bed of at least one catalyst being present in each tube. To regulate the temperature, the tubes are surrounded by a heat transfer medium, for example a salt melt. Despite this thermostatting, it is possible for hotspots in which the temperature is higher than in the remainder of the catalyst bed to occur. These hotspots give rise to secondary reactions such as the total combustion of the starting material or lead to formation of undesirable by-products which can be separated from the reaction product only with difficulty, if at all, for example the formation of phthalide or benzoic acid in the preparation of phthalic anhydride (PA) from o-xylene. Furthermore, the formation of a pronounced hotspot prevents a rapid running-up of the reactor to the reaction temperature of the reaction since the catalyst can be irreversibly damaged above a certain hotspot temperature, so that the loading can be increased only in small steps and has to be monitored very carefully.

To reduce this hotspot, it has become customary in industry to arrange catalysts having different activities in zones in the catalyst bed, with the less active catalyst generally being arranged in the fixed bed so that the reaction gas mixture comes into contact with it first, i.e. it is located toward the gas inlet end of the bed, while the more active catalyst is located toward the gas outlet end of the catalyst bed. The catalysts of differing activity in the catalyst bed can be exposed to the reaction gas at the same temperature, but the two zones of catalysts having differing activities can also be thermostatted to different reaction temperatures for contact with the reaction gas (DE-A 40 13 051).

Catalysts which have proven useful for these oxidation reactions are coated catalysts in which the catalytically active composition is applied in the form of a shell to a support material which is generally inert under the reaction conditions, e.g. quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or a mixture of these support materials. Catalytically active constituents of the catalytically active composition of these coated catalysts are generally titanium dioxide in the form of its anatase modification plus vanadium pentoxide. In addition, the catalytically active composition may further comprise small amounts of many other oxidic compounds which, as promoters, influence the activity and selectivity of the catalyst, for example by lowering or increasing its activity. Examples of such promoters are the alkali metal oxides, in particular lithium, potassium, rubidium and cesium oxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. Promoters which reduce the activity and increase the selectivity are, for example, the alkali metal oxides, while oxidic phosphorus compounds, in particular phosphorus pentoxide, increase the activity of the catalyst but reduce its selectivity.

According to the processes of DE-A 16 42 938 and DE-A 17 69 998, such coated catalysts are produced by spraying an aqueous and/or organic solvent-containing solution or suspension of the constituents of the active composition and/or their precursor compounds, which is hereinafter referred to as a "slurry", onto the support material in a heated coating drum at elevated temperature until the amount of active composition as a proportion of the total weight of the catalyst has reached the desired value. According to DE 21 06 796, the coating procedure can also be carried out in fluidized-bed coaters as are described, for example, in DE 1280756. However, spraying in a coating drum and coating in a fluidized bed result in high losses since considerable amounts of the slurry are converted into a mist or parts of the active composition which has already been applied are rubbed off again by abrasion and are carried out by the waste gas. Since the proportion of active composition in the total catalyst should generally have only a small deviation from the prescribed value because the amount of active composition applied and the thickness of the shell strongly influence the activity and selectivity of the catalyst, the production methods indicated require the catalyst to be cooled, taken from the coating drum or the fluidized bed and weighed at frequent intervals to determine the amount of active composition applied. If too much active composition is deposited on the catalyst support, it is generally not possible to carry out a subsequent, careful removal of the excess active composition without adversely affecting the strength of the shell, in particular without crack formation in the catalyst shell.

To reduce these problems, it has become customary in industry to add organic binders, preferably copolymers, advantageously in the form of an aqueous dispersion, of vinyl acetate/vinyl laurate, vinyl acetate/acrylate, styrene/acrylate, vinyl acetate/maleate and vinyl acetate/ethylene, to the slurry. The amounts of binder used are 10–20% by weight, based on the solids content of the slurry (EP-A 744 214). If the slurry is applied to the support without using organic binders, coating temperatures above 150° C. are advantageous. When the abovementioned binders are added, the usable coating temperatures are, depending on the binder used, from 50 to 450° C. (DE 21 06 796). The binders applied burn off within a short time after introduction of the catalyst into the reactor and start-up of the reactor. The addition of binder has the additional advantage that the active composition adheres well to the support so that transport and charging of the catalyst are made easier.

Gas-phase oxidations over the abovementioned coated catalysts do not take place only on the outer surface of the shell. To achieve the catalyst activity and selectivity required for complete conversion of the high loadings of the reaction gas with starting material employed in industrial processes, it is necessary for the total active composition shell of the catalyst to be utilized efficiently and thus for the reaction centers located in this shell to be readily accessible to the reaction gas. Since the oxidation of aromatic compounds to give carboxylic acids and/or carboxylic anhydrides proceeds via many intermediates and the desired product can be further oxidized over the catalyst to form carbon dioxide and water, optimum matching of the residence time of the reaction gas in the active composition by generating a suitable active composition structure (for example its porosity and pore radius distribution) in the catalyst shell is necessary to achieve a high conversion of starting material while at the same time suppressing the oxidative degradation of the desired product.

Furthermore, it has to be taken into account that the gas composition at the outer surface of the active composition shell does not necessarily correspond to the gas composition at points inside the active composition. Rather, it is to be expected that the concentration of primary oxidation products is higher and the starting material concentration is correspondingly lower than at the outer catalyst surface. This different gas composition should be taken into account by means of a targeted variation of the composition of the active shell within this shell in order to achieve optimum catalyst activity and selectivity. Thus, DE 22 12 964 has already described a method of sequentially spraying slurries of differing compositions onto a support and the use of the catalysts obtained in this way for preparing phthalic anhydride.

However, the multilayer coated catalysts obtained in this way do not yet give satisfactory results and have the disadvantage that only unsatisfactory yields of phthalic anhydride are achieved when they are used for the oxidation of o-xylene.

It is an object of the present invention to propose multilayer coated catalysts which allow a further increase in the selectivity of the oxidation of aromatic hydrocarbons to form carboxylic acids.

We have found that this object is achieved by a coated catalyst for the catalytic gas phase oxidation of aromatic hydrocarbons, comprising, on an inert nonporous support, a catalytically active composition comprising, in each case based on the total amount of catalytically active composition, from 1 to 40% by weight of vanadium oxide, calculated as $V_2O_5$, from 60 to 99% by weight of titanium dioxide, calculated as $TiO_2$, up to 1% by weight of a cesium compound, calculated as Cs, up to 1% by weight of a phosphorus compound, calculated as P, and up to a total of 10% by weight of antimony oxide, calculated as $Sb_2O_3$, wherein the catalytically active composition is applied in two or more layers, where the inner layer or inner layers have an antimony oxide content of from 1 to 15% by weight and the outer layer has, in contrast, an antimony oxide content which is from 50 to 100% lower and the amount of catalytically active composition of the inner layer or the inner layers is from 10 to 90% by weight of the total amount of catalytically active composition.

We have also found a production process for these catalysts and a process using these catalysts for preparing carboxylic acids and/or anhydrides and especially phthalic anhydride.

The thickness of the inner layer or the sum of the thicknesses inner layers is generally from 0.02 to 0.2 mm, preferably from 0.05 to 0.1 mm, and that of the outer layer is generally from 0.02 to 0.2 mm, preferably from 0.05 to 0.1 mm.

The novel catalysts preferably comprise two concentric layers of catalytically active composition, where the inner layer preferably comprises from 2 to 10, in particular from 5 to 10% by weight, of vanadium oxide and preferably from 2 to 7, in particular from 2.5 to 5% by weight, of antimony oxide and the outer layer preferably comprises from 1 to 5, in particular from 2 to 4% by weight, of vanadium oxide and preferably from 0 to 2, in particular from 0 to 1% by weight, of antimony oxide.

In addition, the coated catalysts comprise further constituents which are known per se for the oxidation of aromatic hydrocarbons to carboxylic acids, for example titanium dioxide in the anatase form having a BET surface area of from 5 to 50 $m^2/g$, preferably from 13 to 28 $m^2/g$.

The nonporous inert support comprises, for example, quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or a mixture of these support materials. Preference is given to using steatite in the form of spheres having a diameter of from 3 to 6 mm or of rings having an external diameter of from 5 to 9 mm and a length of from 4 to 7 mm.

Apart from the optional additives cesium and phosphorus which have already been mentioned above, it is in principle possible for the catalytically active composition to further comprise small amounts of many other oxidic compounds which, as promoters, influence the activity and selectivity of the catalyst, for example by lowering or increasing its activity. Examples of such promoters are the alkali metal oxides, in particular lithium, potassium and rubidium oxides as well as the abovementioned cesium oxide, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide and cerium oxide. However, from among this group, cesium is generally used as promoter. Further preferred additives from among the abovementioned promoters are the oxides of niobium, tungsten and lead in amounts of from 0.01 to 0.50% by weight, based on the catalytically active composition. Suitable additives for increasing the activity but reducing the selectivity are, especially, oxidic phosphorus compounds, in particular phosphorus pentoxide.

In general, the inner layer of the catalyst is phosphorus-containing and the outer layer is low in phosphorus or phosphorus-free.

The application of the individual layers of the coated catalyst on the inert nonporous support can be carried out using any methods known per se, for example by (a) spraying-on of solutions or suspensions in a coating drum, (b) coating with a solution or suspension in a fluidized bed or (c) powder coating of the supports.

With regard to (a)

The sequential spraying-on is generally carried out as described in DE 22 12 94 and EP 21325, with the proviso that chromatographic effects, i.e. the migration of individual constituents into the other layer, should be avoided as far as possible. If the active components to be applied are not at least partly present as insoluble metal compounds, it may be advantageous for this purpose to subject the powders to be applied to a thermal pretreatment or to make them virtually insoluble in another way, e.g. by means of additives.

With regard to (b)

The coating in a fluidized bed can be carried out as described in DE 12 80 756.

With regard to c)

The method of powder coating, which is known from WO-A 98/37967 and EP-A 714 700, can also be employed for sequential coating in a plurality of layers. For this purpose, powders are first prepared from the solution and/or suspension of the catalytically active metal oxides, with or without addition of auxiliaries, and these powders are applied in succession, with or without heat treatment in between, in the form of a shell to the support.

To remove volatile constituents, the catalyst is generally, at least afterwards, subjected to a heat treatment.

The novel catalysts are generally suitable for the gas-phase oxidation of aromatic $C_6$–$C_{10}$-hydrocarbons such as benzene, the xylenes, toluene, naphthalene or durene (1,2,4,5-tetramethylbenzene) to give carboxylic acids and/or carboxylic anhydrides, e.g. maleic anhydride, phthalic anhydride, benzoic acid and/or pyromellitic dianhydride.

In particular, the novel coated catalysts make possible a significant increase in the selectivity and yield in the preparation of phthalic anhydride.

For this purpose, the catalysts produced according to the present invention are introduced into reaction tubes which are thermostatted from the outside to the reaction temperature, for example by means of salt melts, and the reaction gas is passed over this catalyst bed at temperatures of generally from 300 to 450, preferably from 320 to 420 and particularly preferably from 340 to 400° C., and a gauge pressure of generally from 0.1 to 2.5, preferably from 0.3 to 1.5 bar, and at a space velocity of generally from 750 to 5000 $h^{-1}$.

The reaction gas fed to the catalyst is generally produced by mixing a gas comprising molecular oxygen and, if appropriate, suitable reaction moderators or diluents, e.g. steam, carbon dioxide and/or nitrogen, with the aromatic hydrocarbon to be oxidized. The gas comprising the molecular oxygen generally comprises from 1 to 100, preferably from 2 to 50 and particularly preferably from 10 to 30 mol %, of oxygen, from 0 to 30, preferably from 0 to 10 mol %, of water vapor, from 0 to 50, preferably from 0 to 1 mol %, of carbon dioxide and nitrogen as balance. To produce the reaction gas, the gas comprising molecular oxygen is generally mixed with from 30 to 150 g of the aromatic hydrocarbon to be oxidized per standard $m^3$ of gas.

In carrying out the gas-phase oxidation, it is advantageous to thermostat two or more zones, preferably two zones, of the catalyst bed located in the reaction tube to different reaction temperatures, for which purpose it is possible to use, for example, reactors having separate salt baths, as described in DE-A 22 01 528 or DE-A 28 30 765. If the reaction is carried out in two reaction zones, as described in DE-A 40 13 051, the reaction zone located toward the end at which the reaction gas enters, which zone generally makes up from 30 to 80 mol % of the total catalyst volume, is generally thermostatted to a reaction temperature which is from 1 to 20 higher, preferably from 1 to 10 and in particular from 2 to 8° C. higher, than that of the reaction zone located toward the gas outlet end. Alternatively, the gas-phase oxidation can also be carried out at one reaction temperature without division into temperature zones. Regardless of the temperature structure, it has been found to be particularly advantageous to use catalysts which differ in their catalytic activity and/or the chemical composition of their active shell in the abovementioned reaction zones of the catalyst bed. When using two reaction zones, the catalyst used in the first reaction zone, i.e. that located toward the end at which the reaction gas enters, is preferably one which has a somewhat lower catalytic activity than the catalyst located in the second reaction zone, i.e. the reaction zone located toward the gas inlet end. In general, the reaction is controlled by the temperature profile so that the major part of the aromatic hydrocarbon present in the reaction gas is reacted at maximum yield in the first zone.

If the preparation of PA is carried out using the catalysts of the present invention and a plurality of reaction zones in which different catalysts are present, the novel coated catalysts can be used in all reaction zones. However, considerable advantages over conventional processes can generally be achieved even if a coated catalyst according to the present invention is used only in one of the reaction zones of the catalyst bed, for example the first reaction zone, and coated catalysts produced in a conventional way are employed in the other reaction zones, for example the second or last reaction zone.

EXAMPLES

The anatase employed contains: 0.18% by weight of S, 0.08% by weight of P, 0.24% by weight of Nb, 0.01% by weight of Na, 0.01% by weight of K, 0.004% by weight of Zr, 0.004% by weight of Pb.

Example 1

Production of Coated Catalyst Ia—Comparison

A suspension comprising 250.0 g of anatase having a BET surface area of 20 $m^2/g$, 13.6 g of vanadyl oxalate (=7.98 g of $V_2O_5$), 1.37 g of cesium sulfate (=1.01 g of Cs), 940 g of water and 122 g of formamide was dried in a spray dryer at a gas inlet temperature of 280° C. and a gas outlet temperature of the drying gas (air) of 120° C. to produce 270 g of powder having a particle size of from 3 to 60 µm for 90% by weight of the powder. After calcination of the powder (1 hour at 400° C.), 90 g of the calcined powder were mixed with 10 g of melamine. 700 g of steatite (magnesium silicate) rings having an external diameter of 8 mm, a length of 6 mm and a wall thickness of 1.5 mm were coated with 93 g of the melamine-containing powder with addition of 56 g of a mixture of 30% by weight of water and 70% by weight of glycerol in a coating drum at 20° C. for 20 minutes. The catalyst support which had been coated in this way was subsequently dried at 25° C. After heat treatment at 400° C. for ½ hour, the weight of the catalytically active composition applied in this way was 10.7% by weight, based on the total weight of the finished catalyst. The catalytically active composition which had been applied, i.e. the catalyst shell, comprised 0.40% by weight of cesium (calculated as Cs), 3.0% by weight of vanadium (calculated as $V_2O_5$) and 96.6% by weight of titanium dioxide.

Example 2

Production of Coated Catalyst Ib—Comparison

The procedure of Example 1 was repeated, but using a suspension comprising 400.0 g of anatase having a BET surface area of 21 $m^2/g$, 57.6 g of vanadyl oxalate (=33.8 g of $V_2O_5$), 2.75 g of cesium sulfate (=2.02 g of Cs), 14.4 g of antimony trioxide, 2.5 g of ammonium dihydrogen phosphate (=0.67 g of P), 1500 g of water and 196 g of formamide. The catalytically active composition applied comprised 0.15% by weight of phosphorus (calculated as P), 7.5% by weight of vanadium (calculated as $V_2O_5$), 3.2% by weight of antimony (calculated as $Sb_2O_3$), 0.45% by weight of cesium (calculated as Cs) and 89.05% by weight of titanium dioxide.

Example 3

Production of Coated Catalyst Ic—Comparison

The procedure of Examples 1 and 2 was repeated, except that 46 g of the powder described in Example 1 were applied to the support first and 47 g of the powder described in Example 2 were applied subsequently.

Example 4

Production of Coated Catalyst Id—Comparison 700 g of steatite (magnesium silicate) rings having an external diameter of 8 mm, a length of 6 mm and a wall thickness of 1.5 mm were heated to 160° C. in a coating drum and sprayed with a suspension comprising 400.0 g of anatase having a BET surface area of 20 m$^2$/g, 57.6 g of vanadyl oxalate (=33.8 g of V$_2$O$_5$), 14.4 g of antimony trioxide, 2.5 g of ammonium dihydrogen phosphate (=0.67 g of P), 2.44 g of cesium sulfate (=1.79 g of Cs), 618 g of water and 128 g of formamide until the weight of the layer applied was 10.5% of the total weight of the finished catalyst. The catalytically active composition applied in this way, i.e. the catalyst shell, comprised, on average, 0.15% by weight of phosphorus (calculated as P), 7.5% by weight of vanadium (calculated as V$_2$O$_5$), 3.2% by weight of antimony (calculated as Sb$_2$O$_3$), 0.4% by weight of cesium (calculated as Cs) and 89.05% by weight of titanium dioxide.

Example 5

Production of Catalyst IIa—According to the Present Invention

The procedure of Example 3 was repeated, except that 46 g of the powder described in Example 2 were applied to the support first and 47 g of the powder described in Example 1 were applied subsequently.

Example 6

Production of Catalyst IIb—According to the Present Invention

The procedure of Example 5 was repeated, but with the modification that the powder prepared as described in Example 2 comprised 61.5 g instead of 57.6 g of vanadyl oxalate.

Example 7

Production of Catalyst IIc—According to the Present Invention

The procedure of Example 5 was repeated, but with the modification that the powder prepared as described in Example 2 comprised 20.02 g instead of 14.4 g of antimony trioxide.

Example 8

Production of Catalyst IId—According to the Present Invention

The procedure of Example 5 was repeated, but with the modification that the powder prepared as described in Example 2 comprised 9.0 g instead of 14.4 g of antimony oxide.

Example 9

Production of Catalyst IIe—According to the Present Invention 700 g of steatite (magnesium silicate) rings having an external diameter of 8 mm, a length of 6 mm and a wall thickness of 1.5 mm were heated to 160° C. in a coating drum and sprayed with a suspension comprising 400.0 g of anatase having a BET surface area of 20 m$^2$/g, 57.6 g of vanadyl oxalate (=33.8 g of V$_2$O$_5$), 14.4 g of antimony trioxide, 2.5 g of ammonium dihydrogen phosphate (=0.67 g of P), 2.44 g of cesium sulfate (=1.79 g of Cs), 618 g of water and 128 g of formamide until the weight of the layer applied was 5.3% of the total weight of the finished catalyst. These precoated rings were subsequently sprayed with a suspension comprising 400.0 g of anatase having a BET surface area of 20 m$^2$/g, 30.7 g of vanadyl oxalate, 2.45 g of cesium sulfate, 618 g of water and 128 g of formamide until the weight of the layer applied was 10.6% of the total weight of the finished catalyst.

Example 10

Production of Catalyst III—Not According to the Present Invention 700 g of steatite (magnesium silicate) rings having an external diameter of 8 mm, a length of 6 mm and a wall thickness of 1.5 mm were heated to 160° C. in a coating drum and sprayed with a suspension comprising 400.0 g of anatase having a BET surface area of 20 m$^2$/g, 57.6 g of vanadyl oxalate, 14.4 g of antimony trioxide, 2.5 g of ammonium dihydrogen phosphate, 0.61 g of cesium sulfate, 618 g of water and 128 g of formamide until the weight of the layer applied was 10.5% of the total weight of the finished catalyst. The catalytically active composition applied in this way, i.e. the catalyst shell, comprised 0.15% by weight of phosphorus (calculated as P), 7.5% by weight of vanadium (calculated as V$_2$O$_5$), 3.2% by weight of antimony (calculated as Sb$_2$O$_3$), 0.1% by weight of cesium (calculated as Cs) and 89.05% by weight of titanium dioxide.

Example 11

Preparation of PA—According to the Present Invention and Comparison

An iron tube having a length of 3.85 m and an internal diameter of 25.2 mm was charged with 1.30 m of catalyst III and subsequently with 1.60 m of one of the catalysts Ia–Id or IIa–IIe. To regulate the temperature, the iron tube was surrounded by a salt melt. 4.0 standard m$^3$/h of air having loadings of 98.5% by weight purity o-xylene of from 0 to about 85 g/standard m$^3$ of air were passed through the tube from the top downward. At a loading of 75–85 g, the results summarized in the following table were obtained (yield=the amount of PA obtained in % by weight, based on 100%-pure o-xylene).

| Catalyst | layer (O = outer; I = Inner) | V₂O₅ (% by weight) | Sb₂O₃ (% by weight) | Cs (% by weight) | P (% by weight) | TiO₂ (% by weight) | Salt bath temperature (°C.) | PA yield (% by weight) | Phthalide content of the crude PA (% by weight) |
|---|---|---|---|---|---|---|---|---|---|
| Ia comp. | O = I | 3.0 | | 0.40 | | 96.6 | 350–352 | 113.2 | 0.17 |
| Ib comp. | O = I | 7.5 | 3.2 | 0.45 | 0.15 | 88.7 | 357–359 | 113.5 | 0.30 |
| Ic comp. | O | 7.5 | 3.2 | 0.45 | 0.15 | 88.7 | 357–360 | 112.9 | 0.16 |
|  | I | 3.0 | | 0.40 | | 96.6 | | | |
| Id comp. | O = I | 7.5** | 3.2 | 0.40 | 0.15 | 88.7 | 360–361 | 112.5 | 0.15 |
| IIa | O | 3.0 | | 0.40 | | 96.6 | 353–354 | 114.2 | 0.13 |
|  | I | 7.5 | 3.2 | 0.45 | 0.15 | 88.7 | | | |
| IIb | O | 3.0 | | 0.40 | | 96.6 | 354–355 | 114.6 | 0.18 |
|  | I | 8.0 | 3.2 | 0.45 | 0.15 | 88.7 | | | |
| IIc | O | 3.0 | | 0.40 | | 96.6 | 355–356 | 114.0 | 0.20 |
|  | I | 8.0 | 4.5 | 0.45 | 0.15 | 88.7 | | | |
| IId | O | 3.0 | | 0.40 | | 96.6 | 354–355 | 114.1 | 0.15 |
|  | I | 8.0 | 2.0 | 0.45 | 0.15 | 88.7 | | | |
| IIe | O | 4.0** | | 0.40 | | 95.6 | 352–353 | 114.6 | 0.19 |
|  | I | 7.5** | 3.2 | 0.40 | 0.15 | 88.7 | | | |

*Due to abrasion effects during the coating procedure, there is no abrupt change in chemical composition between the two layers, but rather there is a gradual transition from one chemical composition to the other; in the extreme case, traces of the active powder of the inner layer are also present in the outer layer. Further constituents of the active composition which can be detected by analysis and originate from impurities in the anatase used are not shown.
**As a result of the production method, chromatographic effects occur in these examples and lead, depending on the method of drying, to different vanadium concentration profiles; it is therefore only possible to give an average vanadium concentration.

We claim:

1. A coated catalyst for the catalytic gas-phase oxidation of aromatic hydrocarbons, comprising, on an inert nonporous support, a catalytically active composition comprising, in each case based on the total amount of catalytically active composition, from 1 to 40% by weight of vanadium oxide, calculated as $V_2O_5$, from 60 to 99% by weight of titanium dioxide, calculated as $TiO_2$, up to 1% by weight of a cesium compound, calculated as Cs, up to 1% by weight of a phosphorus compound, calculated as P, and a total of from more than 0 up to 10% by weight of antimony oxide, calculated as $Sb_2O_3$, wherein the catalytically active composition is applied in two or more layers, where the inner layer or inner layers have an antimony oxide content of from 1 to 15% by weight and the outer layer has, in contrast, an antimony oxide content which is from 50 to 100% lower, the amount of catalytically active composition of the inner layer or the inner layers is from 10 to 90% by weight of the total amount of catalytically active composition and the amounts of the constituents of the catalytically active composition are to be selected from the stated ranges such that they sum to 100% by weight.

2. A coated catalyst as claimed in claim 1, wherein the catalytically active composition of the inner layer or the sum of the inner layers is from 30 to 70% by weight of the total amount of catalytically active composition of the catalyst.

3. A coated catalyst as claimed in claim 1, wherein the thickness of the inner layer or the sum of the thicknesses of the inner layers is from 0.02 to 0.2 mm and the thickness of the outer layer is from 0.02 to 0.2 mm.

4. A coated catalyst as claimed in claim 1, wherein the catalyst has two concentric layers of catalytically active composition, where the inner layer contains from 2 to 7% by weight of antimony oxide and the outer layer contains from 0 to 2% by weight of antimony oxide.

5. A coated catalyst as claimed in claim 1, wherein the catalyst has two concentric layers of catalytically active composition, where the inner layer contains from 5 to 10% by weight of vanadium oxide and the outer layer contains from 1 to 5% by weight of vanadium oxide.

6. A coated catalyst as claimed in claim 1, wherein the material of the inert nonporous support is steatite.

7. A coated catalyst as claimed in claim 1, wherein the titanium oxide therein is present as titanium dioxide in the anatase form and has a BET surface area of from 13 to 28 $m^2/g$.

8. A coated catalyst as claimed in claim 1, wherein two concentric layers of catalytically active composition are applied in the form of a shell to an inert nonporous steatite support, where, apart from titanium dioxide in the anatase form having a BET surface area of from 13 to 28 $m^2/g$, the inner layer comprises from 5 to 10% by weight of vanadium oxide, calculated as $V_2O_5$, and from 2 to 7% by weight of antimony oxide, calculated as $Sb_2O_3$, and the outer layer comprises from 1 to 5% by weight of vanadium oxide, calculated as $V_2O_5$, and from 0 to 2% by weight of antimony oxide, calculated as $Sb_2O_3$.

9. A process for producing coated catalysts as claimed in claim 1, which comprises applying two or more than two layers of the catalytically active composition in succession to an inert nonporous support by spraying.

10. A process for producing coated catalysts as claimed in claim 1, which comprises applying two or more than two layers of the catalytically active composition in succession to an inert nonporous support by coating with the binder-containing catalytically active composition in powder form.

11. A process for preparing carboxylic acids and/or carboxylic anhydrides by the partial oxidation of aromatic hydrocarbons which comprises contacting an aromatic hydrocarbon with gases containing molecular oxygen in the presence of a catalyst as defined in claim 1.

12. A process for preparing phthalic anhydride by the partial oxidation of o-xylene and/or naphthalene which comprises contacting o-xylene and/or naphthalene with gases containing molecular oxygen in the presence of a catalyst as defined in claim 1.

* * * * *